United States Patent
Barnard et al.

(10) Patent No.: US 8,187,643 B2
(45) Date of Patent: May 29, 2012

(54) SHAMPOO FORMULATION FOR TREATMENT OF HAIR LOSS AND METHOD OF USE

(76) Inventors: Robert A. Barnard, Ventura, CA (US); Ted William Steininger, Ventura, CA (US); Greg Steininger, legal representative, Oak Park, CA (US)

( * ) Notice: Subject to any disclaimer, the term of this patent is extended or adjusted under 35 U.S.C. 154(b) by 1051 days.

(21) Appl. No.: 12/079,380

(22) Filed: Mar. 26, 2008
(Under 37 CFR 1.47)

(65) Prior Publication Data
US 2009/0087498 A1    Apr. 2, 2009

Related U.S. Application Data

(60) Provisional application No. 60/920,759, filed on Mar. 28, 2007.

(51) Int. Cl.
*A61K 36/10* (2006.01)
*A61K 36/8962* (2006.01)
*A61K 125/00* (2006.01)
*A61P 17/14* (2006.01)
*A61Q 7/00* (2006.01)

(52) U.S. Cl. .......... 424/754; 424/717; 514/881

(58) Field of Classification Search .......... None
See application file for complete search history.

(56) References Cited

U.S. PATENT DOCUMENTS

| 1,350,843 | A | * | 8/1920 | Roman ............... 424/74 |
| 5,624,672 | A | | 4/1997 | Bathurst et al. |
| 5,759,548 | A | | 6/1998 | Bathurst et al. |
| 6,306,398 | B1 | | 10/2001 | Bathurst et al. |
| 2005/0069598 | A1 | | 3/2005 | Ribnicky et al. |
| 2005/0142116 | A1 | | 6/2005 | Higuchi |
| 2006/0115556 | A1 | | 6/2006 | Foulger et al. |

FOREIGN PATENT DOCUMENTS

| CH | 682217 | A5 | * | 8/1993 |
| DE | 3332055 | | | 3/1985 |
| DE | 3332055 | A1 | * | 3/1985 |
| EP | 0173181 | | | 3/1986 |
| JP | 61068425 | | | 4/1986 |
| JP | 61093109 | | | 5/1986 |
| JP | 61178910 | | | 8/1986 |
| JP | 2048514 | | | 2/1990 |
| JP | 2005289850 | A | * | 10/2005 |
| KR | 2002078547 | A | * | 10/2002 |
| WO | WO 9850005 | | | 11/1998 |

OTHER PUBLICATIONS

Benitez, Vanesa, et al., Characterization of Industrial Onion Wastes (*Allium cepa* L.): Dietary Fibre and Bioactive Compounds, Plant Foods for Human Nutrition, Feb. 12, 2011, Springer Science+Business Media, LLC.

* cited by examiner

*Primary Examiner* — Ernst Arnold
*Assistant Examiner* — Christopher R Lea
(74) *Attorney, Agent, or Firm* — Cislo & Thomas, LLP

(57) ABSTRACT

A shampoo formulation comprising a shampoo, bicarbonate soda, and onion skins used alone or in combination with a conditioner comprising acetic acid for the treatment of hair loss and promotion of hair growth.

24 Claims, No Drawings

SHAMPOO FORMULATION FOR TREATMENT OF HAIR LOSS AND METHOD OF USE

CROSS-REFERENCE TO RELATED APPLICATION

This patent application claims the benefit of U.S. Provisional Patent Application Ser. No. 60/920,759, filed Mar. 28, 2007, which application is incorporated here by this reference.

BACKGROUND OF THE INVENTION

1. Technical Field

This invention relates to shampoo formulations used to treat hair loss.

2. Background Art

Most people, to some degree, will experience balding, or alopecia, sometime in their lives. Some estimate that 35 million men in the United States are affected by male pattern baldness or androgenetic alopecia. In general, it appears that the incidence of male pattern baldness correlates with one's age. For example, men in their twenties have a twenty percent incidence of male pattern baldness, those in their thirties have a thirty percent incidence, while those in their forties have a forty percent incidence and so on. One study showed the prevalence of mid-frontal hair loss increases with age and affects 57% of women and 73.5% of men aged 80 and over.

Pattern baldness, or androgenetic alopecia, affecting approximately, one-third of men and women, is the most common type of hair loss. Pattern baldness is characterized by a typical pattern of receding hairline and hair thinning on the crown and can begin as early as the teen years. In men, hair loss begins at the temples and crown and ends with partial or complete baldness. In women, hair loss is generally limited to thinning at the front, sides or crown with complete baldness rarely occurring.

Another type of alopecia, alopecia areata, can be temporary. It can involve hair loss on your scalp or other parts of your body. With alopecia areata, baldness usually occurs in small, round, smooth patches.

Each hair sits in a cavity in the skin called a follicle. The average human head has about 100,000 hair follicles. Each follicle can grow about 20 individual hairs in a person's lifetime. Hair grows about an inch every couple of months. Each hair grows for 2 to 6 years, remains at that length for a short period, then falls out. Most people shed 50 to 150 hairs a day. A new hair soon begins growing in its place.

Baldness in men occurs when the rate of shedding exceeds the rate of regrowth or when the follicle shrinks over time, resulting in shorter and finer hair. Eventually, the shrunken hair follicle may be completely devoid of hair inside, thus failing to grow new hair. Even though the follicles are small, they remain alive, suggesting the possibility of new growth.

Although the mechanism is not clearly understood, genetics and hormones are thought to be involved in pattern baldness. In pattern baldness, heredity appears to play a significant role as pattern baldness on either side of the family increases risk of balding. Excessive amounts of a hormone known as dihydrotestosterone ("DHT") is also thought to adversely affect hair follicles. DHT binds to androgen receptors in the hair follicles to regulate normal hair growth. Testosterone, a hormone that is present in high levels in males after puberty, is converted to DHT by an enzyme called 5-alpha reductase. As men mature, their bodies produce more testosterone resulting in increased amounts of DHT. Androgen receptor activity increases, slowing down hair production and producing weaker, shorter hair each time the hair regrows.

Other causes of temporary hair loss include disease, diabetes, lupus and thyroid disorder, poor nutrition, medications, certain drugs, medical treatments, childbirth, hair treatments and scalp infections.

Baldness, whether permanent or temporary, cannot be cured. But treatments are available to help promote hair growth or hide hair loss. However, results vary and side effects can be disconcerting.

Minoxidil (Rogaine), available over-the-counter, is a liquid that you rub into your scalp twice daily to regrow hair and to prevent further loss. Some people experience some hair regrowth or a slower rate of hair loss or both. However, new hair resulting from minoxidil use may be thinner and shorter than previous hair. In addition, side effects can include irritation of the scalp.

Finasteride (Propecia) is a prescription medication to treat male-pattern baldness taken daily in pill form. Finasteride inhibits the production of the male hormone dihydrotestosterone. Many people taking finasteride experience a slowing of hair loss, and some may show some new hair growth. Results may take up to several months to manifest. Side effects may include diminished sex drive and sexual function. In addition, Finasteride is not approved for use by women. In fact, it poses significant danger to women of childbearing age and should not be handled by pregnant women.

Surgical procedures, such as hair transplants and scalp reduction surgery, have also been used to treat hair loss. Hair transplants involve taking tiny plugs of skin, each containing one to several hairs, and implanting them into the balding areas. However, effective treatment may require several sessions. Scalp reduction involves decreasing the area of bald skin by surgically removing a balding area and closing the gap with hair-covered scalp. However, these surgical procedures are expensive, can be painful, and may require several procedures. In addition, risks include infection and scarring.

Thus, a safe, effective, cost-effective, easy treatment for preventing hair loss or promoting hair growth is still needed.

BRIEF SUMMARY OF INVENTION

The present invention is directed toward shampoo formulations for preventing hair loss and stimulating hair growth. The formulation is a mixture of shampoo, bicarbonate soda and onion skins used in combination with a conditioner containing acetic acid. The use of the shampoo formulation is used similar to that of a typical shampoo and conditioner.

DETAILED DESCRIPTION OF THE INVENTION

The detailed description set forth below is intended as a description of presently-preferred embodiments of the invention and is not intended to represent the only forms in which the present invention may be formulated or utilized. The description sets forth the functions and the sequence of steps for formulating and using the invention. However, it is to be understood that the same or equivalent functions and sequences may be accomplished by different embodiments that are also intended to be encompassed within the spirit and scope of the invention.

The present invention encompasses a shampoo formulation for treating hair loss, a method of preparing a shampoo formulation for treating hair loss, and a method for treating hair loss.

In one embodiment the shampoo formulation is composed of at least two parts or mixtures. One mixture is referred to as a bicarbonate shampoo mixture. A second mixture is referred to as an onion skin shampoo mixture. A third, optional mixture is referred to as an acetic acid conditioner mixture. The bicarbonate shampoo mixture is combined with the onion skin shampoo mixture to create a bicarbonate/onion skin mixture. The bicarbonate/onion skin mixture and the acetic acid conditioner are stored separately and used in series with each other as the shampoo formulation for treating hair loss.

The bicarbonate/onion skin mixture comprises bicarbonate soda of approximately 5% to approximately 20% by weight, a shampoo being present in an amount of approximately 70% to approximately 95% by weight, and an onion skin being present in an amount of approximately 0.1% to approximately 10% by weight. Preferably, the bicarbonate soda is approximately 8% to approximately 9% by weight, the shampoo is approximately 85% to approximately 90% by weight, and the onion skin is approximately 1% to approximately 8% by weight. The bicarbonate/onion skin mixture is created first by creating the bicarbonate shampoo mixture and the onion skin shampoo mixture separately, then combining the bicarbonate shampoo mixture and the onion skin shampoo mixture together.

The bicarbonate shampoo mixture is formulated by combining a first portion of the shampoo with the bicarbonate soda. Preferably, approximately 70% to approximately 95% of the shampoo in the bicarbonate/onion skin mixture is used in preparing the bicarbonate shampoo mixture. More preferably, approximately 80% of the shampoo is used in preparing the bicarbonate shampoo mixture. In a preferred embodiment, the bicarbonate shampoo comprises approximately 3% to approximately 25% bicarbonate soda and approximately 75% to approximately 97% shampoo. Preferably the bicarbonate shampoo comprises approximately 5% to approximately 20% bicarbonate soda by weight and approximately 80% to approximately 95% shampoo by weight. More preferably the bicarbonate shampoo comprises approximately 10% to approximately 12% bicarbonate soda by weight and approximately 88% to approximately 90% shampoo by weight. This bicarbonate shampoo mixture should be stirred slowly and the bicarbonate soda should be folded into the shampoo. The bicarbonate shampoo mixture should be allowed to sit for approximately 24 hours. Any excess shampoo may be removed or siphoned off. The bicarbonate shampoo mixture may then be re-stirred, for example with a paddle mixer, and allowed to sit.

The onion skin shampoo is prepared by combining a second portion of the shampoo with the onion skin. Preferably, approximately 5% to approximately 30% of the shampoo used in making the bicarbonate/onion skin mixture is used in preparing the onion skin shampoo. More preferably, approximately 20% of the shampoo used in preparing the bicarbonate/onion skin mixture is used in preparing the onion skin shampoo. In a preferred embodiment, the onion skin shampoo mixture comprises approximately 10% to approximately 30% onion skin by weight and approximately 70% to approximately 90% shampoo by weight. Preferably, the onion skin is approximately 20% by weight and the shampoo is approximately 80% by weight. The shampoo is first brought to a slow rolling boil. Onion skins are then added to the boiling shampoo. Brown onion skins are preferable; however, yellow onion skins are also acceptable. White, purple, red and other types of onion skins may also be used. Preferably, the onion skin is added in a cheese cloth to facilitate removal of the onion skins at a later time. After the onion skins have been added, the heat may be turned down and the onion skin mixture may simmer or stew for approximately 30 minutes. After approximately 30 minutes, the onion skins may be removed. If a cheese cloth was used, then removing the cheese cloth would easily remove the onion skins.

The bicarbonate/onion skin mixture comprises approximately 15% to approximately 30% onion skin shampoo by weight and approximately 70% to approximately 85% bicarbonate shampoo by weight. Preferably, the bicarbonate/onion skin shampoo comprises approximately 20% to approximately 25% onion skin shampoo by weight and 75% to approximately 80% bicarbonate shampoo by weight. The onion skin shampoo mixture should be slowly stirred and folded into the bicarbonate shampoo mixture. This results in the creation of the bicarbonate/onion skin shampoo, which should be allowed to stand for approximately 8 to 12 hours prior to use. Any excess liquid or shampoo may be removed.

The optional acetic acid conditioner comprises a conditioner present in an amount of approximately 90% to approximately 99% by weight and an acetic acid present in an amount of approximately 1% to approximately 10% by weight. Preferably, the acetic acid conditioner comprises approximately 95% to approximately 98% conditioner by weight and approximately 2% to approximately 5% acetic acid by weight. The acetic acid conditioner is created separately and stored separately from the bicarbonate/onion skin mixture.

In another embodiment of this invention the shampoo formulation is composed of two parts or mixtures. One mixture is referred to as a baking soda shampoo mixture. The second mixture is referred to as an onion skin mixture. The baking soda shampoo mixture is combined with the onion skin mixture to create a baking soda/onion skin shampoo.

The baking soda/onion skin shampoo comprises a baking soda present in an amount of approximately 1% to approximately 10% by weight; a shampoo present in an amount of approximately 20% to approximately 40% by weight, a water present in an amount of approximately 40% to approximately 70% by weight, and an onion skin present in an amount of approximately 0.5% to approximately 20% by weight. The baking soda/onion skin shampoo is created first by creating the baking soda shampoo mixture and the onion skin mixture separately, then combining the baking soda shampoo mixture and the onion skin mixture together.

The baking soda shampoo mixture is created by combining and mixing approximately 10% to approximately 20% baking soda by weight with approximately 80% to approximately 90% by weight shampoo. Preferably, the baking soda shampoo comprises approximately 14% to approximately 16% baking soda by weight and approximately 84% to approximately 86% shampoo by weight. This baking soda shampoo mixture may be stirred 1 to approximately 50 times for approximately every 1 to 10 minutes during the first four hours. Preferably, the baking soda shampoo mixture may be stirred approximately 5 to approximately 6 times for approximately every 3 minutes, during the first 4 hours. The baking soda shampoo mixture should be allowed to sit for approximately 24 hours prior to combining with the onion skin mixture.

The onion skin mixture is created by combining the water and the onion skin. The onion skin mixture should be approximately 0.5% to approximately 13% onion skin by weight and approximately 85% to approximately 99.5% water by weight. The onion skin mixture should be boiled and stirred for at least 2 minutes, then simmered on low to medium heat, and stirred 1 to 50 times during approximately a 1 to 2 hour period. Preferably, the onion skin mixture is stirred approximately 6 to 10 times.

The baking soda/onion skin shampoo is created by adding the baking soda shampoo mixture to the onion skin mixture while the onion skin mixture is still hot. The baking soda/onion skin shampoo is stirred for approximately 1 hour then allowed to stand for approximately 18 to 24 hours prior to use.

Treating hair loss generally includes the steps involved in using a typical shampoo and conditioner during a shower or hair wash. In one embodiment a user typically begins by wetting his hair and scalp with water. Any excess water may be removed from the hair. As an optional step, a therapeutically effective amount of the acetic acid conditioner may be applied to the hair and scalp. The amount necessary will vary based on the size of scalp and the degree of balding. However, in general, approximately one teaspoonful to approximately one tablespoonful may be used. If the user feels inadequate coverage over the scalp or balding area, an additional amount may be applied to sufficiently cover the desired balding area. Preferably the acetic acid conditioner should be massaged into the scalp.

Next, the scalp may be covered for approximately 1 to approximately 10 minutes with a wet, warm towel, a shower cap, or any other covering to prevent the conditioner from drying out. Preferably, the scalp may be covered for approximately 4 to approximately 5 minutes with a wet, warm towel, a shower cap, or any other covering. The acetic acid conditioner may then be rinsed off. Any excess water may again be removed from the hair.

Next, a therapeutically effective amount of the bicarbonate/onion skin shampoo may be applied to the hair and scalp. The amount necessary will vary based on the size of scalp and the degree of balding. However, in general, approximately one teaspoonful to approximately one tablespoonful may be used. Again, if the user feels inadequate coverage over the scalp or balding area, an additional amount may be applied to sufficiently cover the desired balding area. Preferably the bicarbonate/onion skin shampoo should be scrubbed into the scalp, for example, with the fingertips or fingernails, for approximately 1 to approximately 10 minutes, or some other sufficient time to form a lather. Preferably, the bicarbonate/onion skin shampoo should be scrubbed into the scalp for approximately 3 to approximately 4 minutes. A small nail brush may also be used in place of the finger nails.

Once the lather has been formed and the scalp has been scrubbed, the bicarbonate/onion skin shampoo may be left on for approximately 5 to approximately 30 minutes. Preferably, the bicarbonate/onion skin shampoo is left on for approximately 15 to approximately 20 minutes. The bicarbonate/onion skin shampoo should not be allowed to dry out. This may be accomplished by adding a sufficient amount of bicarbonate/onion skin shampoo as necessary to keep the hair and scalp moist. Alternatively or additionally, the scalp may be covered, for example, with a wet, warm towel, a shower cap, or the like. Next, the bicarbonate/onion skin shampoo may be rinsed thoroughly.

Optionally, a therapeutically effective amount of the acetic acid conditioner may be re-applied and allowed to sit for approximately 30 seconds to approximately 5 minutes. Preferably, the acetic acid conditioner sits for approximately 1 to approximately 2 minutes. The acetic acid conditioner may then be rinsed off. This process may be repeated every day up to once a week. Preferably, application of the bicarbonate/onion skin shampoo formulation is every other day or 3 days per week.

In another embodiment a user may begin by wetting the hair and scalp. Any excess water may be squeezed or toweled off, leaving the hair and scalp damp. A therapeutically effective amount of the baking soda/onion skin shampoo may be applied to the hair and scalp, particularly on the balding or thinning area. Preferably, approximately one teaspoonful to approximately one tablespoon of the baking soda/onion skin shampoo may be applied to the hair and scalp, particularly on the balding or thinning area. The precise amount of the baking soda/onion skin shampoo will vary based on the size of the scalp and the degree of balding. The baking soda/onion skin shampoo may be scrubbed into the hair and scalp with the fingertips or fingernails using a scratching/scrubbing motion for approximately 1 to approximately 10 minutes to stimulate the scalp. Preferably, the baking soda/onion skin shampoo is scrubbed in for approximately 2 to 5 minutes. The baking soda/onion skin shampoo may be left on for approximately 1 minute to approximately 30 minutes, preferably 5 to 20 minutes. Longer periods will produce more pronounced results. During this time the hair and scalp should be kept damp. This may be accomplished by applying more of the baking soda/onion skin shampoo as necessary. Additionally or alternatively, a wet, warm towel, shower cap, or the like may be used to cover the hair and scalp. After the baking soda/onion skin shampoo is allowed to sit, water may be added and the hair and scalp shampooed further. The baking soda shampoo may then be rinsed thoroughly. This process may be repeated from once a day to once a week. Preferably the process is repeated every other day or three times per week.

EXAMPLES

Formulation 1

A bicarbonate shampoo mixture was created by mixing 4 ounces of a bicarbonate soda with 32 fluid ounces of a Thrifty's Extra Balsam & Protein Shampoo, extra body formula. This was allowed to sit for approximately 24 hours. The excess amount of the shampoo was removed. The mixture was re-stirred with a paddle mixer and allowed to sit.

The onion skin shampoo mixture was created by slowly boiling 8 ounces of shampoo and adding 48 brown onion skins in a cheese cloth. The heat was turned down to low and the onion skins were stewed in the shampoo for approximately 30 minutes. The onion skins were then removed.

Eight ounces of the onion skin shampoo mixture was slowly stirred and folded into the bicarbonate shampoo mixture and allowed to stand for 8 hours to create the bicarbonate/onion skin shampoo. The excess liquid was siphoned off.

The acetic acid conditioner was created by taking 32 ounces of Thrifty's Extra Balsam+Protein instant Conditioner, extra body formula and adding 1 tablespoon of distilled acetic acid and mixing well.

Formulation 2

A baking soda shampoo mixture was created by combining approximately 5.5 to 6 ounces of baking soda with approximately 32 to 34 fluid ounces of Suave—Balancing with Balsam and Protein shampoo. The baking soda shampoo was stirred approximately 5 to 6 times for approximately 3 minutes each time, during the first 4 hours. The bicarbonate shampoo mixture was allowed to sit for approximately 20 hours.

The onion skin mixture was created by adding 2 ounces of brown onion skins (approximately 48 onion skins) to approximately 2 quarts of water. This mixture was stirred to a boil for 2 to 3 minutes. The temperature was then reduced to medium and allowed to simmer. While simmering the mixture was stirred approximately 6 to 10 times during a two hour period.

The baking soda shampoo was added to the onion skin mixture while the onion skin mixture was still hot to create the baking soda/onion skin shampoo. The baking soda/onion skin shampoo was stirred slowly approximately 4 to 5 times during the first hour. The baking soda/onion skin shampoo was allowed to stand for approximately 18 to 24 hours.

What is claimed is:

1. A method of preparing a shampoo formulation for treating hair loss, comprising the steps of:
   a. creating a bicarbonate shampoo mixture by
      i) mixing a bicarbonate soda with a first shampoo portion at a ratio of 1:8, respectively,
      ii) allowing the bicarbonate shampoo mixture to sit for approximately 24 hours,
      iii) removing an excess amount of the shampoo that does not mix with the bicarbonate soda, and
      iv) stirring the bicarbonate shampoo mixture;
   b. creating an onion skin shampoo mixture by
      i) boiling a second shampoo portion,
      ii) adding onion skins in cheese cloth at a ratio of 6 onion skins to every ounce of the second shampoo portion,
      iii) simmering the onion skin mixture for approximately 30 minutes, and
      iv) removing the onion skins after the simmering step
   c. mixing the bicarbonate shampoo mixture with the onion skin shampoo mixture to create a bicarbonate/onion skin mixture at a ratio of 4:1, respectively;
   d. allowing the bicarbonate/onion skin mixture to stand for approximately 8 to 12 hours;
   e. removing an excess of shampoo;
   f. creating an acetic acid conditioner by
      i) mixing a conditioner with an acetic acid at a ratio of 64:1, respectively; and
   g. storing the acetic acid conditioner separately from the bicarbonate/onion skin mixture.

2. A shampoo formulation for treating hair loss prepared from a bicarbonate/onion skin mixture, comprising:
   a. a bicarbonate soda being present in an amount of approximately 5% to approximately 20% by weight;
   b. a shampoo being present in an amount of approximately 70% to approximately 95% by weight; and
   c. an onion skin being present in an amount of approximately 0.1% to approximately 10% by weight.

3. The shampoo formulation of claim 2 wherein
   a. the bicarbonate soda is present in an amount of approximately 8% to approximately 9% by weight;
   b. the shampoo is present in an amount of approximately 85% to approximately 90% by weight; and
   c. the onion skin is present in an amount of approximately 1% to approximately 8% by weight.

4. The shampoo formulation of claim 2 being formulated by
   a. combining a first portion of the shampoo with the bicarbonate soda to create a bicarbonate shampoo mixture; and
   b. combining a second portion of the shampoo with the onion skin to create an onion skin shampoo mixture.

5. The shampoo formulation of claim 4 being further formulated by
   a. combining approximately 70% to approximately 95% of the shampoo with the bicarbonate soda to create the bicarbonate shampoo mixture; and
   b. combining approximately 5% to approximately 30% of the shampoo with the onion skin to create the onion skin shampoo mixture.

6. The shampoo formulation of claim 5 being further formulated by
   a. first boiling the shampoo prior to adding the onion skin in creating the onion skin shampoo mixture;
   b. then allowing the onion skin shampoo mixture to simmer for approximately 30 minutes;
   c. allowing the bicarbonate shampoo mixture to sit for approximately 24 hours prior to mixing with the onion skin shampoo mixture; and
   d. mixing the onion skin shampoo mixture with the bicarbonate shampoo mixture.

7. The shampoo formulation of claim 6 being further formulated by allowing the bicarbonate/onion skin mixture to stand for approximately 8 to 12 hours prior to use.

8. The shampoo formulation of claim 7 further comprising an acetic acid conditioner, comprising:
   a. a conditioner present in an amount of approximately 90% to approximately 99% by weight and
   b. an acetic acid present in an amount of approximately 1% to approximately 10% by weight,
   c. wherein the acetic acid conditioner is stored separately from the bicarbonate/onion skin mixture.

9. The shampoo formulation of claim 8 wherein
   a. the conditioner is present in an amount of approximately 95% to approximately 98% by weight; and
   b. the acetic acid is present in an amount of approximately 2% to approximately 5% by weight.

10. A method for treating hair loss, comprising the steps of:
    a. providing the shampoo formulation of claim 8;
    b. applying a therapeutically effective amount of the acetic acid conditioner to the hair and scalp;
    c. applying a wet warm towel to the scalp for approximately 1 to approximately 10 minutes;
    d. rinsing the scalp and hair;
    e. applying a therapeutically effective amount of the bicarbonate/onion skin mixture to the scalp and forming a lather;
    f. allowing the lather to sit for approximately 5 to approximately 30 minutes;
    g. rinsing off the bicarbonate/onion skin mixture from the scalp thoroughly; and
    h. repeating steps (a) - (g) approximately 3 times per week.

11. The method of claim 10 further compromising the steps of:
    a. applying a therapeutically effective amount of the acetic acid conditioner to the scalp, after rinsing off the bicarbonate/onion skin mixture, for approximately 30 seconds to approximately 5 minutes; and
    b. rinsing off the acetic acid conditioner from the scalp.

12. The method of claim 10 further comprising the step of
    a. scrubbing the scalp with the bicarbonate/onion skin mixture with a finger nail or nail brush for approximately 1 to approximately 10 minutes to form a lather after applying the bicarbonate/onion skin mixture to the scalp and prior to allowing the lather to sit.

13. The method of claim 12 further comprising the step of preventing the bicarbonate/onion skin mixture from drying out, while the lather is sitting for approximately 5 to approximately 30 minutes, by adding a sufficient amount of bicarbonate/onion skin mixture to keep the hair and scalp moist.

14. The method of claim 12 further comprising the step of preventing the bicarbonate/onion skin mixture from drying out, while the lather is sitting for approximately 5 to approximately 30 minutes, by covering the hair and scalp.

15. A method of preparing a shampoo for treating hair loss, comprising the steps of:
    a. creating a baking soda shampoo mixture by
       i) combining a baking soda with a shampoo at a ratio of approximately 1:6 to approximately 1:5, respectively,
       ii) stirring the baking soda shampoo mixture approximately every 1 to 10 minutes, during the first 4 hours, iii) allowing the baking soda shampoo mixture to sit for approximately 24 hours;
b. creating an onion skin mixture by
  i) combining water with onion skins at a ratio of approximately 1 quart of water for every approximately 24 onion skins,
  ii) boiling and stirring the onion skin mixture for approximately at least 2 minutes,
  iii) simmering the onion skin mixture on low to medium heat,
  iv) stirring the mixture during a two hour period;
c. mixing the baking soda shampoo with the onion skin mixture while the onion skin mixture is still hot to create a baking soda/onion skin shampoo mixture;
d. stirring the baking soda/onion skin shampoo mixture during a 1 hour period; and
e. allowing the baking soda/onion skin shampoo mixture to stand for approximately 18 to approximately 24 hours.

16. The method of claim 15 further compromising the step of creating an acetic acid conditioner by
  a. mixing a conditioner with an acetic acid at a ratio of approximately 64:1, respectively; and
  b. storing the acetic acid conditioner separately from the baking soda/onion skin shampoo mixture.

17. A shampoo formulation for growing hair prepared from a baking soda/onion skin shampoo, comprising:
  a. a baking soda present in an amount of approximately 1% to approximately 10% by weight;
  b. a shampoo present in an amount of approximately 20% to approximately 40% by weight;
  c. a water present in an amount of approximately 40% to approximately 70% by weight; and
  d. an onion skin present in an amount of approximately 0.5% to approximately 20% by weight.

18. The shampoo formulation of claim 17 being formulated by
  a. combining the baking soda and the shampoo to create a baking soda shampoo mixture; and
  b. combining the water and the onion skin to create an onion skin mixture.

19. The shampoo formulation of claim 18 being further formulated by
  a. stirring the baking soda shampoo mixture every 3 minutes during the first 4 hours, then allowing the baking soda shampoo mixture to sit for approximately 20 hours; and
  b. boiling and stirring the onion skin mixture for at least 2 minutes,
    i) simmering the onion skin mixture on low to medium heat, and
    ii) stirring the mixture during a 2 hour period.

20. The shampoo formulation of claim 19 being further formulated by
  a. adding the baking soda shampoo mixture to the onion skin mixture while the onion skin mixture is still hot to create the baking soda/onion skin mixture;
  b. stirring the baking soda/onion skin shampoo for approximately 1 hour; and
  c. allowing the baking soda/onion skin shampoo to stand for approximately 18 to 24 hours prior to use.

21. A method for treating hair loss comprising the steps of:
  a. providing the shampoo formulation of claim 20;
  b. applying a therapeutically effective amount of the baking soda/onion skin shampoo to a scalp and forming a lather;
  c. allowing the lather to sit for approximately 1 to 30 minutes;
  d. rinsing off the baking soda/onion skin shampoo from the scalp;
  e. repeating steps (a) - (e) approximately 3 times per week.

22. The method of claim 21 further comprising the step of scrubbing the scalp with the baking soda/onion skin shampoo with a finger nail or nail brush for approximately 1 to 10 minutes to form a lather after applying the baking soda/onion skin shampoo to the scalp and prior to allowing the lather to sit.

23. The method of claim 22 further comprising the step of preventing the baking soda/onion skin shampoo from drying out, while the lather is sitting for approximately 1 to approximately 30 minutes, by adding a sufficient amount of the baking soda/onion skin mixture to keep the scalp moist.

24. The method of claim 22 further comprising the step of preventing the baking soda/onion skin mixture from drying out, while the lather is sitting for approximately 1 to approximately 30 minutes, by covering the hair and scalp.

* * * * *